US00PP33108P2

(12) United States Plant Patent
Olesen

(10) Patent No.: US PP33,108 P2
(45) Date of Patent: Jun. 1, 2021

(54) MINIATURE ROSE PLANT NAMED 'POULPAH101'

(50) Latin Name: *Rosa hybrida*
Varietal Denomination: Poulpah101

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 16/873,989

(22) Filed: Sep. 3, 2020

(51) Int. Cl.
*A01H 5/02* (2018.01)
*A01H 6/74* (2018.01)

(52) U.S. Cl.
USPC ..... Plt./116

(58) Field of Classification Search
USPC ..... Plt./101, 116
See application file for complete search history.

(56) References Cited

U.S. PATENT DOCUMENTS

PP30,574 P2 * 6/2019 Kordes ..... A01H 5/02
Plt./116

OTHER PUBLICATIONS

Nolina Nursey website. 2016. https://www.nolina.nl/nl/n/nolina-nurseries-introduces-dazzling-new-patiohit-imolatm/759. retrieved from the internet Nov. 24, 2020. 4 pages. (Year: 2016).*
Poulsen Roser website. 2020. https://www.poulsenroser.dk/en/roses/ShowProduct/78167. retrieved from the internet Nov. 24, 2020. 2 pages. (Year: 2020).*

* cited by examiner

*Primary Examiner* — Susan McCormick Ewoldt
*Assistant Examiner* — Karen M Redden

(57) ABSTRACT

A new garden rose plant of the Miniature class which has abundant, red and near white striped flowers and attractive foliage. This new and distinct variety has shown to be uniform and stable in the resulting generations from asexual propagation.

2 Drawing Sheets

Botanical designation: *Rosa hybrida.*
Variety denomination: 'Poulpah101'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2012 and the resulting seeds were planted in a controlled environment in Fredensborg, Denmark. The new variety, named 'Poulpah101', originated as a single seedling from the stated cross.

The new variety may be distinguished from its male pollen parent and female seed parent primarily by the following characteristics. The male pollen parent plant has near white flowers while the new variety has red and near white striped flowers. The female seed parent plant has red flowers while the new variety has red and near white striped flowers.

The objective of the hybridization of this rose variety was to create a new and distinct variety with unique qualities, such as:

1. Uniform and abundant red and near white striped flowers;
2. Vigorous, but compact growth when propagated on its own roots;
3. Exceptional disease resistance.

This combination of qualities is not present in previously available commercial cultivars of this type, known to the inventor, and distinguish 'Poulpah101' from all other varieties of which we are aware.

As part of the rose development program, Mogens N. Olesen germinated the seeds from the aforementioned hybridization during winter of 2012 and conducted evaluations on the resulting seedlings in a controlled environment in Fredensborg, Denmark. 'Poulpah101' was selected in the spring of 2013 by the inventor as a single plant from the progeny of the aforementioned hybridization.

Asexual reproduction of 'Poulpah101' by rooted cuttings was first done by Mogens N. Olesen in the nursery in Fredensborg, Denmark in July, 2013. This initial and other subsequent asexual propagations conducted in controlled environments have demonstrated that the characteristics of 'Poulpah101' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpah101'.

Specifically illustrated in FIG. 1 of the drawings are open flowers viewed from above and the side, flower petals and sepals detached showing receptacle, pedicel and reproductive flower parts.

Figure 1:
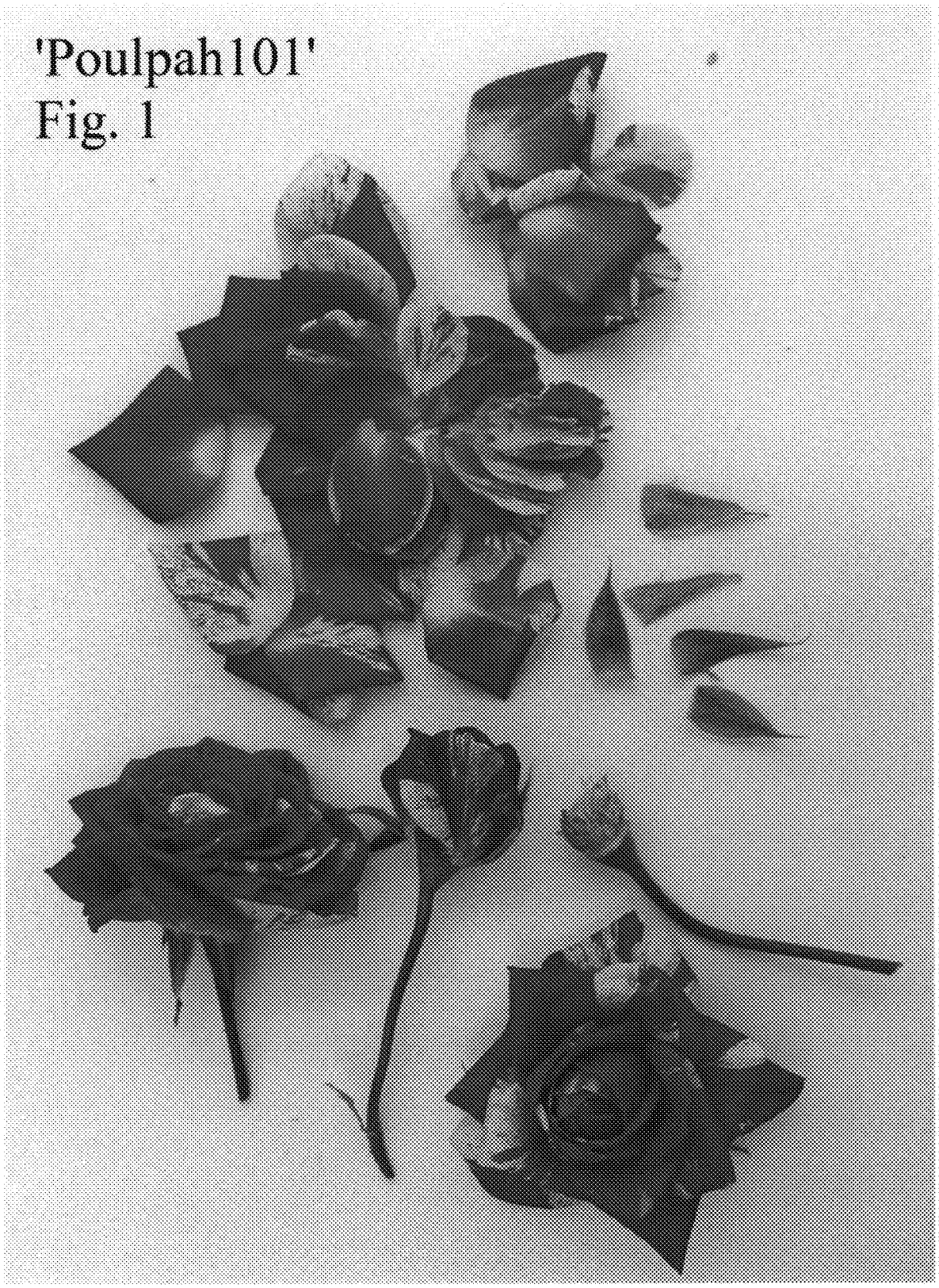
Figure 2:
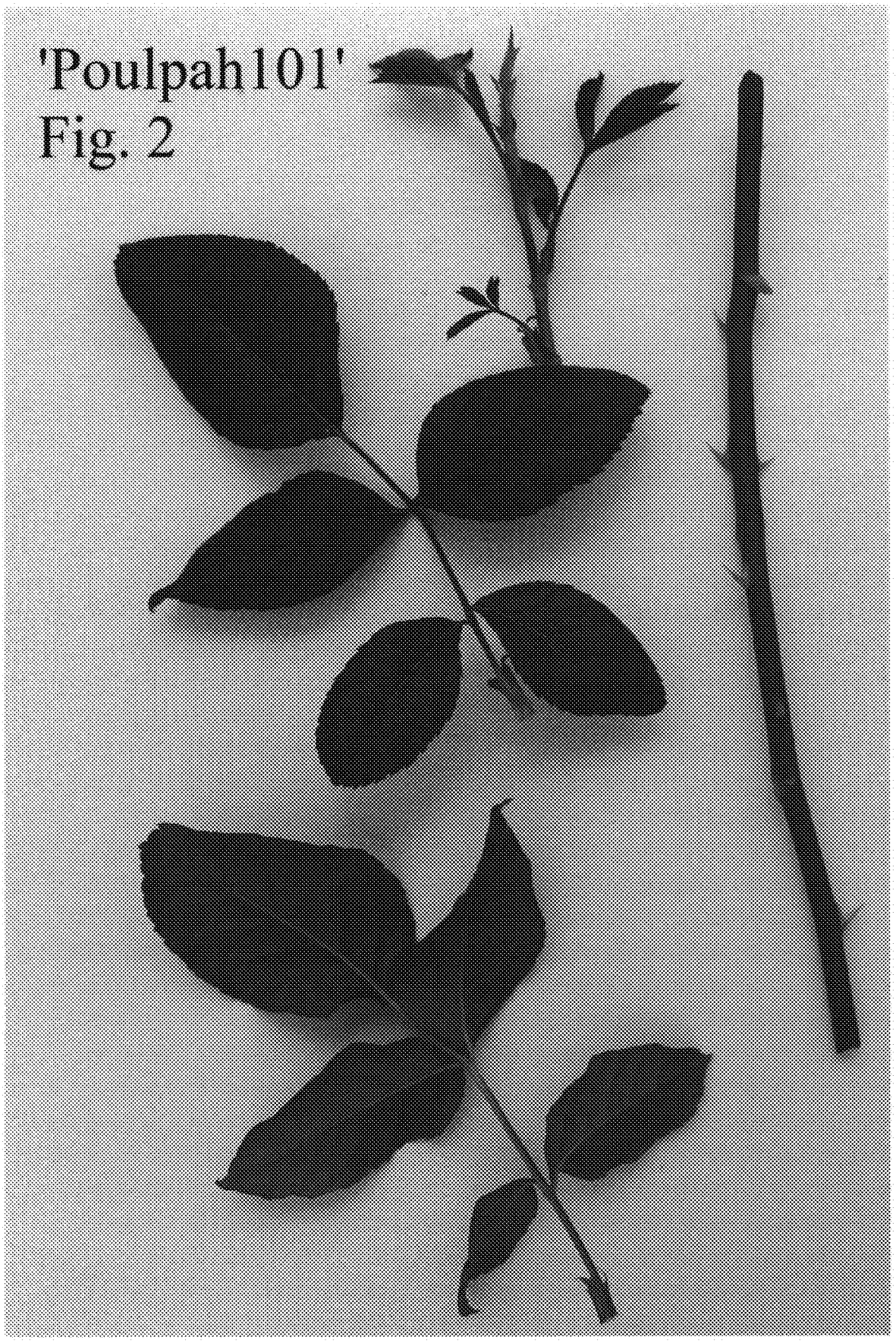

Specifically illustrated in FIG. 2 of the drawings are mature leaves and bare stem, and juvenile growth exhibiting anthocyanin. Plants shown are 4 months of age.

DETAILED DESCRIPTION OF THE VARIETY

The following is a description of 'Poulpah101', as observed in its growth in a controlled environment greenhouse in Odense Denmark. Observed plants are 4 months old and were grown on their own roots in 19 cm containers. Color references are made using The Royal Horticultural Society (London, England) Colour Chart, 2001, except where common terms of color are used.

For a comparison, several physical characteristics of the rose variety 'Poulty019', U.S. Plant Pat. No. 26,051 are compared to 'Poulpah101' in Chart 1.

CHART 1

| | 'Poulpah101' | 'Poulty019' |
|---|---|---|
| Petal Count | 55 | 25 |
| Flower Diameter | 60 mm | 40 mm |
| General Tonality of Flower Color | Red Group 50A with streaks of Yellow Group 11C | Red Group 46A splashed with White N155B & Red49A |

FLOWER AND FLOWER BUD

Blooming habit: Continuous.

Flower bud:

*Size.*—Upon opening, 21 mm in length from base of receptacle to end of bud. Bud diameter is 18 mm.

*Bud form.*—Ovoid.

*Bud color.*—As sepals divide petals are Red Group 46B splashed with Yellow Group 13D.

*Sepal inner surface.*—Color: Yellow-Green Group 146D. Surface: Lightly pubescent.

*Sepal outer surface.*—Color: Yellow-Green Group 144A. Texture: Smooth.

*Sepal shape.*—Apex: Cirrhose. Base: Flat at union with receptacle.

*Sepal margin.*—Margins have weak foliaceous appendages on three of the five sepals.

*Sepal size.*—8 mm long, 10 mm wide.

*Receptacle.*—Texture: Smooth. Size: 8 mm in height, 8 mm wide. Color: Yellow-Green Group 144A. Shape: Funnel.

*Pedicel.*—Surface: Smooth. Length: 52 mm. Diameter: 3 mm on average. Color: Yellow-Green Group 144A. Strength: Strong.

*Peduncle.*—Length: 4 to 5 cm. Diameter: About 4 mm. Color: Yellow-Green Group 144A. Texture: Smooth.

Flower bud development: Flower buds are borne in clusters of 3 to 5 flower buds per stem.

Flower bloom:

*Fragrance.*—Moderate floral scent.

*Duration.*—The blooms have a duration on the plant of approximately 20 days. Petals fall cleanly away from plant after flowers have fully matured.

*Size.*—Flower diameter is 60 mm when open. Flower depth is 30 mm.

*Flower shape.*—High centered, double with a high pointed center which is tightly closed.

*Shape of flower, side view.*—The upper portion is convex. The lower portion is concave.

*Petalage.*—Under normal conditions, flowers have about 55 petals.

General tonality of flower: Open flowers are Red Group 50A with streaks of Yellow Group 11C.

*Petal color.*—Upon opening, outer petals. Upper surface: Red Group 50A and Red-Purple Group N57B splashed with Yellow Group 11C and Yellow Group 10B. At the basal point of attachment, there is a petal spot of Yellow Group 8B. Lower surface: Red Group 53C splashed with Yellow Group 13D. At the basal point of attachment there is a medium sized spot of Yellow Group 10A. Upon opening, inner petals: Upper surface: Red Group 45B splashed with Yellow Group 12C and 12A. Lower surface: Orange-Red Group N34C splashed with Yellow Group 11B. After opening, outer petals. Upper surface: Red Group 50A and Red-Purple Group N57B splashed with Yellow Group 11C and Yellow Group 10B. At the basal point of attachment, there is a petal spot of Yellow Group 8B. Lower surface: Red Group 53C splashed with Yellow Group 13D. At the basal point of attachment there is a medium sized spot of Yellow Group 10A. After opening, inner petals: Upper surface: Red Group 45B splashed with Yellow Group 12C and 12A. Lower surface: Orange-Red Group N34C splashed with Yellow Group 11B. Basal petal spots, after opening: No distinctive coloration at the petal base observed. (or) Upper surface: Lower surface:

Petals:

*Petal reflex.*—Strong.

*Margin.*—Entire and uniform. No undulations.

*Shape.*—Broad and elliptic. Apex shape: Rounded. Base shape: Acute.

*Size.*—35 mm (l)×31 mm (w).

*Texture.*—Smooth.

*Thickness.*—Average.

Petaloids:

*Size.*—20 mm (l) by 14 mm (w).

*Quantity.*—About 10.

*Shape.*—Elliptical, with an acute base and rounded undulated apex.

*Color.*—On the upper side Red Group 45B splashed with strong intonations of Yellow Group 12A. The lower surface is Orange-Red Group N34C splashed with Yellow Group 11B.

Reproductive flower parts:

*Pollen.*—None observed.

*Anthers.*—Size: 3 mm in length. Color: Yellow Group 12C. Quantity: 35 on average.

*Filaments.*—Color: Yellow-Orange Group 14C. Length: 4 mm.

*Pistils.*—Length: 11 mm. Quantity: 18 on average.

*Stigmas.*—Color: Greyed-Yellow Group 160D.

*Styles.*—Color: Greyed-Yellow Group 160D.

*Location of stigmas.*—Superior in location relative to the length of the filaments and the height of the anthers.

*Hips.*—None Observed.

PLANT

Plant growth: Upright. Plants are about 52 cm in height, and 40 cm wide.

Stems:

*Color of juvenile growth*.—Yellow-Green Group 144B.

*Color of mature growth*.—Yellow-Green Group 144A.

*Length*.—Canes are about 23 cm from the base of the plant to the flowering portion.

*Diameter*.—About 5 mm.

*Internodes*.—On mature canes about 50 mm between nodes.

*Surface texture*.—Young wood: Smooth. Older wood: Smooth.

Long prickles:

*Incidence*.—5 prickles per 10 cm of stem.

*Size*.—Average length of prickles on mature stems is 7 mm.

*Shape*.—Upper portion is linear. Lower portion is deep concave.

*Color*.—Juvenile prickles: Greyed-Yellow Group 160B with intonations of Greyed-Red Group 180D. Mature prickles: Greyed-Yellow Group 160B with intonations of Greyed-Red Group 180D Plant foliage:

*Compound leaf*.—142 mm (l)×110 (w).

*Quantity*.—2 leaves per 10 cm of stem on average.

*Leaf bearing angle to the stem*.—45 degrees.

*Color of juvenile foliage*.—Upper side: Yellow-Green Group 144A with intonations of Greyed-Red Group 178A. Lower side: Yellow-Green Group 144B with intonations of Greyed-Red Group 178A.

*Color of mature foliage*.—Upper side: Yellow-Green Group 147A. Lower side: Yellow-Green Group 147B.

Plant leaves and leaflets:

*Stipules*.—Size: 13 mm long, 4 mm wide. Quantity: 2 per compound leaf. Shape: Linear, slightly broad based with outward extending apices. Margins: Finely serrated. Color: Yellow-Green Group 144A.

*Petiole*.—Length: 22 mm. Diameter: 2 mm. Upper surface color: Yellow-Green Group 144A. Lower surface color: Yellow-Green Group 144A.

*Rachis*.—Length: 50 mm. Upper surface color: Yellow-Green Group 144A. Lower surface color: Yellow-Green Group 144A.

*Leaflet*.—Quantity: Normally 5 leaflets. Margins: Serrated. Size: Terminal leaflets are about 70 mm long, 43 mm wide. Shape: Generally elliptical. Base: Rounded. Apex: Acute. Texture: Smooth. Thickness: Average. Arrangement: Odd pinnate. Venation: Reticulate. Glossiness: Not glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Miniature rose class named 'Poulpah101', substantially as illustrated and described herein, due to its abundant red and near white striped flowers, disease resistance, and extended period of bloom.

* * * * *

'Poulpah101'